(12) United States Patent
Fukui et al.

(10) Patent No.: US 9,255,278 B2
(45) Date of Patent: Feb. 9, 2016

(54) POLYNUCLEOTIDE ENCODING PPAT DERIVED FROM JATROPHA AND USE THEREOF

(75) Inventors: Kiichi Fukui, Suita (JP); Joyce Cartagena, Suita (JP); Naoki Wada, Suita (JP); Tsutomu Kohinata, Suita (JP); Yasuhisa Yushio, Osaka (JP); Naoki Ikeguchi, Osaka (JP); Satoshi Tabata, Kisarazu (JP)

(73) Assignees: SUMITOMO ELECTRIC INDUSTRIES, LTD., Osaka (JP); OSAKA UNIVERSITY, Osaka (JP)

( * ) Notice: Subject to any disclaimer, the term of this patent is extended or adjusted under 35 U.S.C. 154(b) by 161 days.

(21) Appl. No.: 13/643,396

(22) PCT Filed: Oct. 25, 2011

(86) PCT No.: PCT/JP2011/074513
§ 371 (c)(1),
(2), (4) Date: Oct. 25, 2012

(87) PCT Pub. No.: WO2012/077421
PCT Pub. Date: Jun. 14, 2012

(65) Prior Publication Data
US 2013/0109874 A1 May 2, 2013

(30) Foreign Application Priority Data

Dec. 8, 2010 (JP) ................................ 2010-273619

(51) Int. Cl.
*A01H 5/00* (2006.01)
*A01H 5/10* (2006.01)
*C12N 15/82* (2006.01)
*C12N 9/06* (2006.01)
*C12N 15/53* (2006.01)
*C12N 9/12* (2006.01)

(52) U.S. Cl.
CPC .......... *C12N 15/8247* (2013.01); *C12N 9/1241* (2013.01); *C12N 15/8243* (2013.01); *C12N 15/8271* (2013.01); *C12N 15/8273* (2013.01); *C12Y 207/07003* (2013.01)

(58) Field of Classification Search
None
See application file for complete search history.

(56) References Cited

U.S. PATENT DOCUMENTS

| | | |
|---|---|---|
| 2005/0214808 A1 | 9/2005 | Umezawa et al. |
| 2007/0174937 A1 | 7/2007 | Umezawa et al. |
| 2008/0040973 A1 | 2/2008 | Nelson et al. |
| 2009/0205079 A1 | 8/2009 | Kumar et al. |

FOREIGN PATENT DOCUMENTS

| | | |
|---|---|---|
| JP | 2005-253395 A | 9/2005 |
| JP | 2009-536029 A | 10/2009 |
| JP | 2009-540830 A | 11/2009 |
| WO | 2008/002480 A2 | 1/2008 |
| WO | 2009/138535 A1 | 11/2009 |
| WO | 2011/125748 A1 | 10/2011 |

OTHER PUBLICATIONS

Akbar et al (European Journal of Scientific Research, vol. 29 No. 3 (2009), pp. 396-403).*
Chen et al (GenBank Accession No. XP_002521564, first available online Aug. 6, 2009).*
International Search Report for PCT/JP2011/058026, mailed Jun. 28, 2011.
Stephenson et al., "Genome-Wide Identification and Expression Analysis of the NF-Y Family of Transcription Factors in *Triticum aestivum*", Plant Mol. Biol., vol. 65, No. 1-2, pp. 77-92, 2007.
Siefers et al., "Tissue-Specific Expression Patterns of *Arabidopsis* NF-Y Transcription Factors Suggest Potential for Extensive Combinatorial Complexity", Plant Physiol., vol. 149, No. 2, pp. 625-641, 2009.
International Search Report for PCT/JP2011/074513, mailed Dec. 6, 2011.
Shibagaki et al., "Genetic engineering of *Jatropha curcas* L. for drought resistance" Dai 61 Kai Abstracts of the Annual Meeting of the Society for Biotechnology, Japan, 2009, 205, 3S2a01, along with an English language translation.
Li et al., "The *Arabidopsis* NFYA5 Transcription Factor is Regulated Transcriptionally and Posttranscriptionally to Promote Drought Resistance" The Plant Cell 20:2238-2251, 2008.
Nelson et al., "Plant Nuclear Factor Y(NF-Y)B Subunits Confer Drought Tolerance and Lead to Improved Corn Yields on Water-Limited Acres" PNAS 104(42):16450-16455, 2007.
Rubio et al., "The Coenzyme A Biosynthetic Enzyme Phosphopantetheine Adenylyltransferase Plays a Crucial Role in Plant Growth, Salt/Osmotic Stress Resistance, and Seed Lipid Storage" Plant Physiol. 148(1):546-556, 2008.
Kupke et al., "4'-Phosphopantetheine and Coenzyme A Biosynthesis in Plants" J. Biol. Chem. 278(40):38229-38237, 2003.
U.S. Appl. No. 13/639,522 to S. Matsunaga et al., filed Oct. 5, 2012.
Sato et al., "Sequence Analysis of the Genome of an Oil-Bearing Tree, *Jatropha curcas* L.", DNA Research, pp. 1-12, Dec. 13, 2010.
Masiero et al., "Ternary Complex Formation between MADS-box Transcription Factors and the Histone Fold Protein NF-YB", The Journal of Biological Chemistry, vol. 277, No. 29, pp. 26429-26435, 2002.
Achten et al., "*Jatropha* Bio-diesel Production and Use", Biomass and Bioenergy, vol. 32, pp. 1063-1084, 2008.
Guo et al., "Protein Tolerance to Random Amino Acid Change", PNAS, vol. 101, No. 25, pp. 9205-9210, 2004.
Requirement for Restriction for U.S. Appl. No. 13/639,522, mailed Mar. 24, 2015.
Office Action issued for U.S. Appl. No. 13/639,522, mailed Jun. 24, 2015.

* cited by examiner

*Primary Examiner* — Lee A Visone
(74) *Attorney, Agent, or Firm* — Greenblum & Bernstein, P.L.C.

(57) ABSTRACT

A PPAT polypeptide of SEQ ID NO: 1 derived from *Jatropha*, a PPAT polynucleotide of SEQ ID NO: 2 and so on were found. By transforming *Jatropha* with these PPAT polynucleotides, it is possible to overexpress the PPAT polypeptide in comparison with a wild type, and biosynthesis of coenzyme A is promoted by these polypeptides, the metabolic function and viability of the transformed *Jatropha* are enhanced, and for example, stress resistance can be significantly improved.

10 Claims, 3 Drawing Sheets

POLYNUCLEOTIDE ENCODING PPAT DERIVED FROM JATROPHA AND USE THEREOF

SEQUENCE LISTING

The instant application contains a Sequence Listing which has been submitted in ASCII format via EFS-Web and is hereby incorporated by reference in its entirety. Said ASCII copy, created on Dec. 4, 2012, is named P42852.txt and is 4,124 bytes in size.

TECHNICAL FIELD

The present invention relates to a polynucleotide encoding phosphopantetheine adenylyltransferase (hereinafter referred to as "PPAT") which is a novel gene of *Jatropha*, and use thereof, and in particular, use thereof for creating stress resistant *Jatropha* with enhanced growth.

BACKGROUND ART

*Jatropha curcas* attracts attention as biological resources for production of biodiesel fuel because it is able to produce a non-edible *Jatropha* oil. Further, *Jatropha* is known as a plant that can be cultivated even at locations unsuited for growth of other crops in terms of water and inorganic nutrients, and is believed to be very beneficial for effective utilization of semi-arid regions and for greening. On the other hand, although *Jatropha* plants grow in barrens, production efficiency of oils by natural cultivating is not high because fruition of the plants is once a year and the size of the fruit is significantly smaller than that of palm. For this reason, development of highly productive *Jatropha* is demanded.

As one measure for improving the production efficiency of a *Jatropha* oil, a method of transforming *Jatropha* so that acetyl CoA carboxylase (ACCase) can be overexpressed for increasing the oil content of the seed is known, for example, as proposed in PTL 1.

On the other hand, from the view point of enhancement of growth of *Jatropha* itself, it is also conceivable to impart environmental stress resistance that ensures high viability even in an environment of water shortage or the like.

As an environmental stress resistant gene recombinant plant, the one wherein the stress responsive signaling intensity and mechanism are modified so as to be adaptive or responsive to environmental stresses such as dry stress, a method for improvement to achieve overproduction of a protein molecule involved in resistance (a protein responding to environmental stresses) and the like are conceivable.

For example, NPL 1 reports, regarding a mechanism of controlling dry stress resistance in *Arabidopsis thaliana*, that a NF-YA5 transcription factor is ABA-dependent and is strongly induced by dry stress, and that transformed *Arabidopsis thaliana* overexpressing NF-YA5 is superior to wild-type *Arabidopsis thaliana* in resistance to dry stress.

Here, abscisic acid (ABA) is a plant hormone that is involved in seed dormancy, opening/closing of stoma and osmotic stress resistance, and ABA is known to be deeply involved in expression of a group of stress responsive genes.

As a method of preparing environmental stress resistant *Arabidopsis thaliana*, PTL 2 proposes a method of utilizing an activating function of a group of genes under the control of a transcription factor that activates transcription by binding with a cis element existing upstream the gene encoding a stress responsive protein expressed due to an environmental stress (a stress responsive transcription factor). Concretely, a SRK2C gene is disclosed as a novel gene encoding a signaling factor that induces expression of DREB/CBF which is a stress responsive transcription factor, and also it is disclosed that *Arabidopsis thaliana* transformed to overexpress the SRK2C gene shows dominantly high survival rate in comparison with a control even after stopping of water supply.

Further, NPL 2 reports that a corn NF-YB factor was identified, and a corn transformed by using this showed higher productivity under the condition of water shortage in comparison with the wild type.

Also, NPL 3 reports about *Arabidopsis thaliana* that nutrient growth and seed yield significantly decrease in an individual wherein the gene encoding phosphopantetheine adenylyltransferase (PPAT) is broken (a ppat-1 mutant) (FIG. 2), while on the contrary, in an individual overexpressing PPAT (an OE strain), the effect of enhancing salts resistance and osmotic resistance (test using mannitol) is obtained in comparison with the wild type, and growth is promoted in comparison with the wild type (see FIGS. 3 and 4).

The PPAT used herein, which is also abbreviated as AtCoaD, is an enzyme involved in biosynthesis of coenzyme A. Coenzyme A is biosynthesized from pantothenic acid as shown in FIG. 1, and PPAT catalyzes an exchange reaction between 4'-phosphopantetheine and dephospho coenzyme A. Coenzyme A consists of pantothenic acid, adenosine diphosphate and 2-thioxy ethaneamine, and is represented by the chemical formula $C_{21}H_{36}P_3N_7O_{16}S$. This participates in a variety of metabolic reactions by binding of an acyl group of various compounds to its terminal thiol group by a thioester bond. Representatively, it is a coenzyme that is involved in the TCA cycle functioning commonly in prokaryotic and eukaryotic cells.

CITATION LIST

Patent Literature

PTL 1: Japanese National Patent Publication No. 2009-536029
PTL 2: Japanese Patent Laying-Open No. 2005-253395

Non Patent Literature

NPL 1: Wen-Xue Li et al., "The *Arabidopsis* NFYA5 Transcription Factor Is Regulated Transcriptionally and Post-transcriptionally to Promote Drought Resistance", The Plant Cell, Vol. 20: 2238-2251 (2008)
NPL 2: Donald E. Nelson et al., "Plant nuclear factor Y(NF-Y)B subunits confer drought tolerance and lead to improved corn yields on water-limited acres", PNAS, vol. 104, No. 42, 16450-16455 (2007)
NPL 3: Rubio S. et al., "The coenzyme A biosynthetic enzyme phosphopantetheine adenylyltransferase plays a crucial role in plant growth, salt/osmotic stress resistance, and seed lipid storage." Plant Physiol., 148: 546-556 (2008)

SUMMARY OF INVENTION

Technical Problem

Since a mechanism of signaling pathway for growth of a plant and environmental stresses in a plant is complicated, various transformation methods have been proposed for creating a plant that is excellent in productivity and environmental stress resistance as described above. However, as to *Jatropha*, a regulatory protein related with stress, a functional protein related with resistance and the like have not been clarified, and information about transformed *Jatropha* having excellent viability is not found.

An object to be achieved by the present invention is to create stress resistant *Jatropha* having excellent viability, and thus to provide a gene or the like capable of transforming wild type *Jatropha* to have excellent viability and stress resistance.

Solution to Problem

For achieving the aforementioned object, as a result of examination on a gene for transforming *Jatropha* to have excellent viability and stress resistance, the inventors of the present invention succeeded in isolating and identifying a polynucleotide encoding phosphopantetheine adenylyltransferase (PPAT) of *Jatropha* which is one of enzymes involved in biosynthesis of coenzyme A, and accomplished the present invention. Specifically, the present invention is as follows.

[1] An isolated polynucleotide selected from the following polynucleotides:

(a) a polynucleotide having a nucleotide sequence represented by SEQ ID NO: 2; and (b) a polynucleotide having a nucleotide sequence having a homology of 90% or higher with the nucleotide sequence of the polynucleotide of (a), wherein a polypeptide encoded thereby maintains stress resistance of the polypeptide encoded by the polynucleotide of (a).

[2] The polynucleotide as described in [1], having a nucleotide sequence represented by SEQ ID NO: 2.

[3] An isolated PPAT polypeptide selected from the following polypeptides:

(a) a polypeptide having an amino acid sequence represented by SEQ ID NO: 1; and (b) a polypeptide having an amino acid sequence having a homology of 90% or higher with the amino acid sequence of the polypeptide of (a), wherein the polypeptide maintains stress resistance of the polypeptide of (a).

[4] The PPAT polypeptide as described in [3], having an amino acid sequence represented by SEQ ID NO: 1.

[5] A polynucleotide encoding the polypeptide as described in [3] or [4].

[6] A *Jatropha* plant transformation vector, wherein the polynucleotide as described in [1], [2] or [5] is incorporated.

[7] A transformant containing the vector as described in [6].

[8] A *Jatropha* plant transformed by using the vector as described in [6], the plant being stress resistant transformed *Jatropha* capable of overexpressing a PPAT polypeptide compared with a wild type.

[9] A seed harvested from the stress resistant transformed *Jatropha* as described in [8].

[10] A method of producing a *Jatropha* oil by squeezing the seed as described in [9] and purifying it.

[11] A *Jatropha* oil produced by the production method as described in [10].

Advantageous Effects of Invention

When *Jatropha* is transformed by using the polynucleotide according to the present invention, the transformed *Jatropha* allows expression of PPAT polypeptide derived from *Jatropha* of the present invention, or a polypeptide equivalent thereto. Biosynthesis of coenzyme A is promoted by these polypeptides, and the metabolic function and viability of the transformed *Jatropha* are enhanced, and for example, stress resistance can be improved significantly.

DESCRIPTION OF EMBODIMENTS

Figure 1:
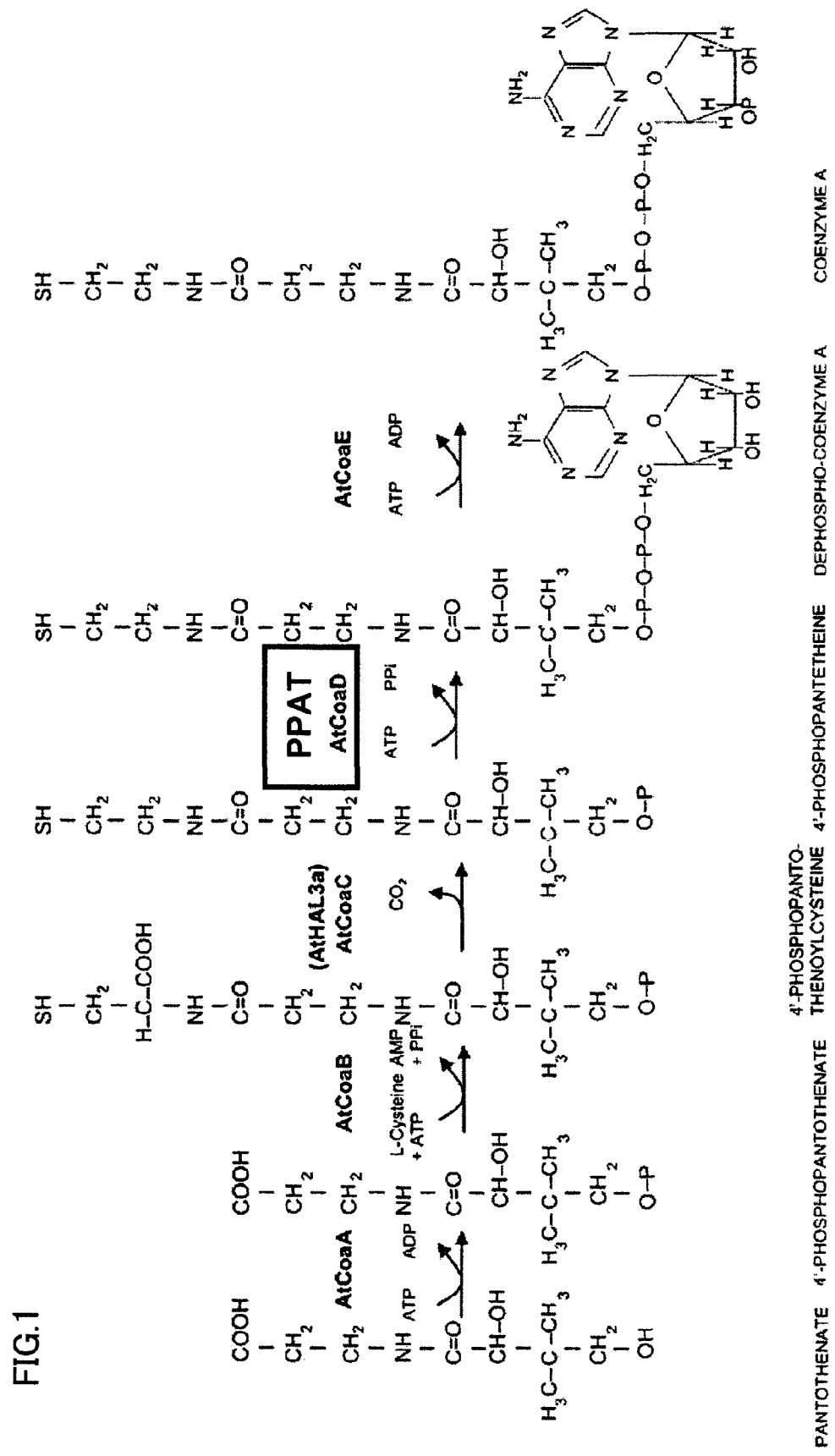
FIG. 1 shows a biosynthesis pathway of coenzyme A from pantothenic acid in a plant (*Arabidopsis thaliana*) (reprinted from Kupke T et al., "4-Phosphopantetheine and Coenzyme A Biosynthesis in Plants" J. Biol. Chem., 278: 38229-38237 (2003)).

[JcPPAT Polypeptide and JcPPAT Gene Encoding the Same]

An isolated novel *Jatropha* gene according to the present invention is a polynucleotide encoding phosphopantetheine adenylyltransferase (PPAT) of *Jatropha*. Concretely, (a) a polynucleotide having a nucleotide sequence represented by SEQ ID NO: 2; and (b) a polynucleotide having a nucleotide sequence having a homology of 90% or higher with the nucleotide sequence of the polynucleotide of (a), wherein a polypeptide encoded thereby maintains stress resistance of the polypeptide encoded by the polynucleotide of (a) (hereinafter, these are collectively referred to as "JcPPAT gene" and so on) are included in the present invention. The nucleotide sequence of the polynucleotide of (b) has a homology of preferably 95% or higher, more preferably 98% or higher, and particularly preferably 99% or higher with the nucleotide sequence of the polynucleotide of (a).

The PPAT polypeptide of the present invention also includes, for example, (a) a polypeptide having an amino acid sequence represented by SEQ ID NO: 1; and (b) a polypeptide having an amino acid sequence having a homology of 90% or higher with the amino acid sequence of the polypeptide of (a), wherein the polypeptide maintains stress resistance of the polypeptide of (a) (hereinafter, these are collectively referred to as "JcPPAT"). The polypeptide of (b) has a homology of preferably 95% or higher, more preferably 98% or higher, and particularly preferably 99% or higher with the amino acid sequence of the polypeptide of (a). The nucleotide sequence of the gene of the present invention also includes polynucleotides encoding the polypeptides of (a) and (b).

As the JcPPAT gene according to the present invention, the one encoding the amino acid sequence represented by SEQ ID NO: 1 is preferably recited, and the polynucleotide having a nucleotide sequence represented by SEQ ID NO: 2 is preferred for creation of transformed *Jatropha* because it is derived from a *Jatropha* genome.

While a method of preparing the JcPPAT gene of the present invention is not particularly limited, for example, DNA of SEQ ID NO: 2 corresponding to the PPAT gene derived from *Jatropha* can be obtained from *Jatropha* mRNA as a PCR product of a target polynucleotide (cDNA encoding PPAT) by conducting a RT-PCR reaction using the following primer set (SEQ ID NOs: 3 and 4). Also, the JcPPAT gene may be obtained according to a routine method, and it may be artificially synthesized, for example, by substituting, deleting or adding a predetermined base in DNA of SEQ ID NO: 2 or the like.

[Chemical formula 1]
Forward primer: 5'-AAAAAGCAGGCTCAAAAATGGCGTTATTAGACGAATCTATGGTTAAT-3' (SEQ ID NO: 3)

Reverse primer: 5'-AGAAAGCTGGGTATGCTACTTCTTGTTTTTTCACCTTCTCGG-3' (SEQ ID NO: 4)

mRNA may be prepared by a generally conducted method. For example, after grinding a frozen plant in a mortar or the like, a crude RNA fraction may be extracted and prepared from the obtained ground matter by a glyoxal method, a guanidine thiocyanate-cesium chloride method, a lithium chloride-urea method, a proteinase K-deoxyribonuclease method or the like. Also, a commercially available kit may be used.

A tissue of a plant that is used as a material is not particularly limited and a seed in the course of maturation or a germinating seed, a mature leaf, and other tissues such as a stem may be used. Among these, from a germinating seed where energy production by seed storage lipid metabolism is active, a larger quantity of PPAT mRNA can be obtained. It is supposed that PPAT activity is enhanced for metabolism of lipids stored in a seed because a large amount of energy is required in germination of the seed. It is also supposed that PPAT mRNA can be obtained efficiently in a seed in the course of maturation, because PPAT activity is enhanced for accumulation of lipids. However, when a large quantity of oil is contained in a tissue like a seed or the like, it is preferred to extract RNA after purifying the ground matter.

Determination and confirmation of a nucleotide sequence of an obtained PCR product may be conducted by a conventionally known method, for example, a Maxim-Gilbert chemical modification method or a dideoxynucleotide chain termination method using M13 phage.

[Creation of Stress Resistant Transformed *Jatropha*]

The stress resistant transformed *Jatropha* of the present invention is created by gene introduction of an expression cassette having the JcPPAT gene prepared as described above operably linked with a promoter for expression or expression regulation, into a wild-type *Jatropha*.

The species of *Jatropha* intended by the present invention are not particularly limited, and *Jatropha curcas*, *Jatropha potagurica*, *Jatropha multifida*, *Jatropha berlandieri*, *Jatropha integerrima* and the like may be used. Among these, from the view point of large oil content, *Jatropha curcas* is preferably used.

The gene introduction may be achieved by any method including methods of directly introducing DNA into a cell such as a method of fusing protoplasts, an electroporation method and a gene shotgun method; and methods of indirectly introducing DNA by using *Agrobacterium tumefaciens* or *R. rhizogenes*, and a method of using an *agrobacterium* is preferred. In the following, a transformation method using an *agrobacterium* is described.

An *agrobacterium* is a plant pathogen, and has a Ti plasmid having a region sandwiched between LB (left border) and RB (right border) (a T-DNA (Transferred DNA) region) that can be cut out and inserted into a host genome. When a host plant is infected with an *agrobacterium* having a plasmid incorporating a gene to be introduced, namely JcPPAT cDNA in this T-DNA region, the T-DNA region is cut out, and forms a complex with a protein group encoded by a vir region, and enters a plant cell, and further insertion into a host genome is achieved.

As a transformation method using an *agrobacterium*, a binary vector method is preferred. The binary vector method is a method of inserting a target gene into a plant genome by introducing into an *agrobacterium*, a plasmid having a target exogenous gene incorporated into a T-DNA region of a plasmid having borders (LB and RB) of the T-DNA region, separately from a T-DNA-deficient plasmid of a Ti plasmid (such as pAL4404), and infecting a plant with the *agrobacterium*.

An expression cassette used for creation of transformed *Jatropha* using the binary vector method includes the JcPPAT gene according to the present invention, a promoter for expression of the nucleotide, a marker gene and a reporter gene in the T-DNA region.

As a promoter, a 35S cauliflower mosaic virus promoter, a nopaline synthase (NOS) promoter, and other endosperm-specific promoters such as β phaseolin, napin and ubiquitin can be recited.

As a selection marker gene, a gene that imparts resistance to a selection agent such as an antibiotic or a herbicide is used. Concrete examples thereof include a kanamycin resistant gene, a paromomycin B resistant gene, or a resistant gene against herbicides such as glufosinate and glyphosate. Also usable is a gene that expresses a selection marker enabling visual identification of a transformant, for example, a chromogenic or fluorescent protein such as luciferase or green fluorescent protein (GFP), or a gene that expresses β glucuronidase or GUS for which various chromogenic substrates are known. Such a selection marker may be used also as a reporter gene.

If necessary, an enhancer, a terminator, a tag and the like may further be included. An enhancer is used for improving expression efficiency of a target gene, and for example, an enhancer region including an upstream sequence in a CaMV 35S promoter can be recited. A terminator may be any sequence capable of terminating transcription of a gene transcribed by a promoter, and for example, a terminator of a nopaline synthase (NOS) gene, and a terminator of an octopine synthase (NOS) and a CaMV 35S RNA gene are recited.

As a binary vector for use in transformation of *Jatropha* by the binary vector method, those including the aforementioned expression cassette in a T-DNA region, and concretely, those prepared by incorporating the aforementioned expression cassette into commercially available vectors such as pBI series, pPZP series, pSMA series, and pGWB series may be used. In particular, a binary vector for plant transformation to which a cloning system of Gateway (registered trade name) is applicable is preferred, and as such a vector, pGWB series vectors can be recited. In these pGWB series vectors, a target gene and a reporter are operably linked using a cauliflower mosaic virus (CaMV) 35S promoter as a promoter; a hygromycin resistant gene or a kanamycin resistant gene as a selection marker gene; β-glucuronidase (GUS), green fluorescent protein (GFP), luciferase (LUC), yellow fluorescent protein (YFP), or cyan fluorescent protein (CFP) as a reporter; and 6×His (SEQ ID NO: 7), FLAG, 3×HA, 4×Myc, GST, or T7-epitope as a tag. Further, there are sequences that encode a reporter and a tag for allowing fusion at both the N terminal and the C terminal.

The Gateway (registered trade name) cloning system facilitates construction of an expression vector by using the Gateway (registered trade name) signal (att). In this method, by a reaction (BP reaction) between a donor vector having attP1 and attP2 sequences, and a target gene having attB1 and attB2 sequences added on each terminal, an entry vector having the target gene incorporated therein (having attL1 and attL2 sequences on each terminal) is created, and then by a recombination reaction (LR reaction) between this entry vector and a destination vector having a promoter required for expression incorporated therein (added with attR1 and attR2 sequences), a vector having the target gene inserted therein (expression vector) is created.

Therefore, first, cloned JcPPAT cDNA is allowed to undergo a BP reaction with a donor vector to prepare an entry vector having cloned JcPPAT cDNA incorporated in the donor vector, and then by a LR reaction between the entry vector and a destination vector (pGWB), an expression vector having the target DNA (JcPPAT gene) incorporated therein can be created.

A detailed description for construction of an expression cassette for plant transformation using the Gateway (registered trade name) binary vector (pGWB) is found in Nakagawa et al., "Development of Series of Gateway Binary Vectors, pGWBs, for Realizing Efficient Construction of Fusion Genes for Plant Transformation", Journal of Bioscience and Bioengineering, Vol. 104, No. 1, 34-41 (2007).

The expression vector created as described above (plant transformation vector) can be amplified in *Escherichia coli*. The amplified transformation vector may be introduced into an *agrobacterium* by an electroporation method or the like. The *agrobacterium* into which the expression vector is introduced in this manner is used for transformation of *Jatropha*.

Introduction of a JcPPAT gene into *Jatropha* by infection of an *agrobacterium* having the plant transformation vector can be achieved by using a known method such as a leaf disc method.

Concretely, a bacterial liquid for infection in which an *agrobacterium* is suspended in a MS medium is prepared, and the bacterial liquid and part of *Jatropha* which is a host (preferably, cut pieces of cotyledons, hereinafter referred to as "*Jatropha* leaf pieces") are co-cultivated for about 3 days. The leaf pieces of *Jatropha* are dipped in a MS medium for about 2 days prior to the co-cultivation, and are preferably sonicated. In this way, it is possible to improve the efficiency of introduction. Also preferred is a Sandvortex method that applies vibration to a suspension of an *agrobacterium* into which sand has been added because infectability of the *agrobacterium* is improved.

As a co-cultivation medium, a MS medium or the like incorporating a plant hormone such as 3-indolebutyric acid (IBA) or 6-benzylaminopurine (BA) is used.

Following the co-cultivation, the *Jatropha* leaf pieces are washed, and transferred into a selection medium (containing an antibiotic corresponding to the selection marker gene used in the expression cassette in the transformation vector), and incubated, and then calluses formed in the leaf pieces are cut out, and transferred to a selection medium, and further screening of the transformed *Jatropha* (recombinant cell) is conducted.

As the selection medium, the one prepared by adding an antibiotic (kanamycin, hygromycin) which is a substance for selection to the medium (MS medium or the like) used for pre-culture, which contains IBA, BA or the like as a plant hormone is preferably used.

Next, the selected calluses are transferred into a medium such as a Root induction (RI) medium or a MS medium, and allowed to root and redifferentiate into a plantlet. Induction of redifferentiation can be achieved by appropriately setting kinds and quantities of various ingredients including plant growth regulation substances such as auxin and cytokinin, and carbon sources in the medium, and light, temperature and so on.

[Transformed *Jatropha*]

Figure 2:
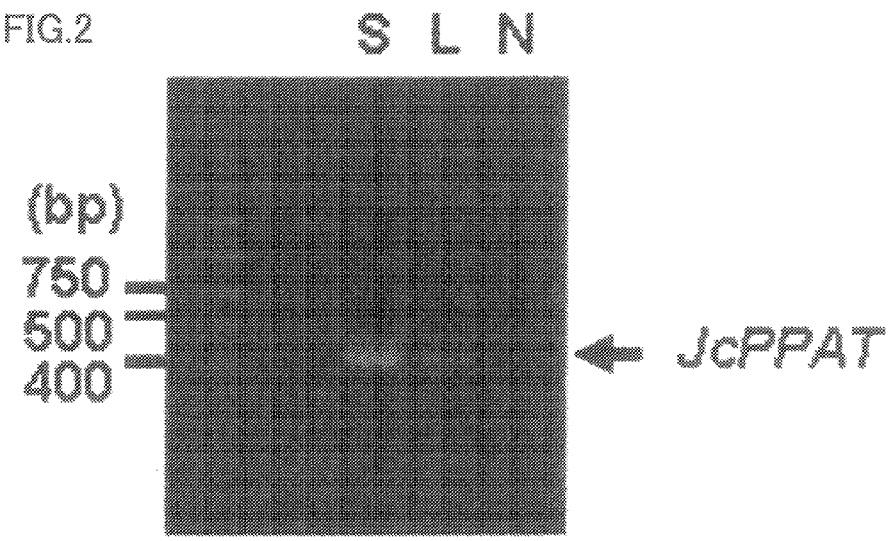
FIG. 2 is a picture showing a result of gel electrophoresis of JcPPAT cDNA in the example.
Figure 3:
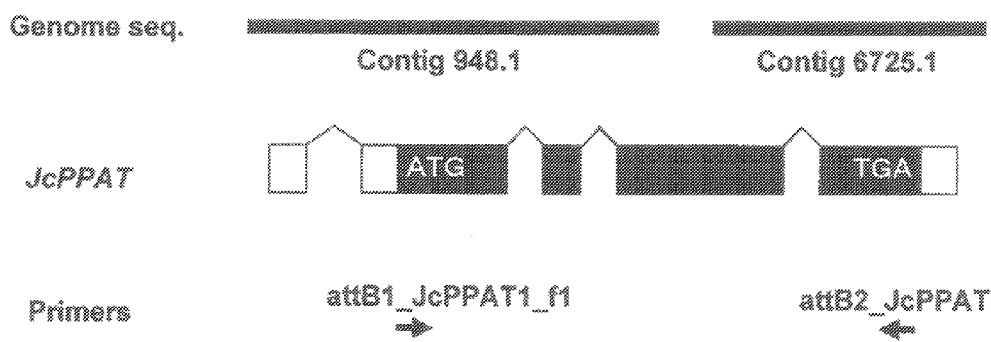
FIG. 3 shows a relationship between a *Jatropha* genome and a JcPPAT gene amplified by a PCR method.
Figure 4:
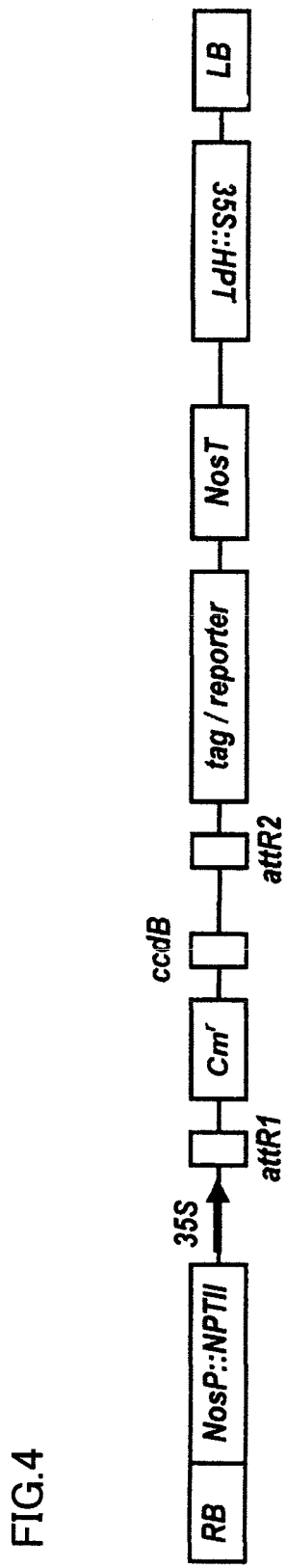
FIG. 4 is a gene map of a pGWB11 plasmid (see Nakagawa et al., "Development of Series of Gateway Binary Vectors, pGWBs, for Realizing Efficient Construction of Fusion Genes for Plant Transformation", Journal of Bioscience and Bioengineering, Vol. 104 (2007), No. 1, p. 38).

Since the transformed *Jatropha* of the present invention has a larger amount of a JcPPAT gene encoding PPAT which is one of the enzymes involved in a synthesis reaction of coenzyme A involved in various metabolic reactions in a cell, compared with the wild type, it is supposed that the PPAT can be overexpressed, and synthesis of coenzyme A is promoted in the transformed *Jatropha* in comparison with the wild type. As disclosed in the aforementioned NPL 3, it is reported that in *Arabidopsis thaliana*, an individual overexpressing PPAT (OE) showed an increased concentration of coenzyme A in comparison with the wild type, and the effect of enhancing salts resistance and osmotic resistance (test using mannitol) was obtained, and growth of plant was enhanced (FIGS. 2 to 4). Similarly, in the transformed *Jatropha* of the present invention, by overexpression of PPAT, the concentration of coenzyme A is increased, and thus the effect of enhancing and promoting salts, osmotic and dry stress resistances and growth can be expected. Thus, increase in yield of seeds can be expected.

Further, in NPL 3, it is reported that in a strain overexpressing PPAT, the oil content of a seed increased by 30 to 50%, and change in fatty acid composition was also observed. Therefore, also in the transformed *Jatropha* of the present invention, it is expected that the oil content of a seed increases, and a fruit having a fatty acid composition different from that of the wild type is obtained.

The transformed plant of the present invention embraces not only "T1 generation" subjected to the transformation treatment, but also progeny plants including "T2 generation" which are succeeding generations obtained from a seed of this plant, and a next generation (T3 generation) obtained by self-fertilization of a flower of the plant of "T2 generation" which is proved to be a transformant by drug selection or analysis by a Southern method or the like.

[Production of *Jatropha* Oil]

A *Jatropha* oil can be produced from a seed harvested from the transformed *Jatropha* of the present invention according to a routine method. For example, a *Jatropha* oil that can be used as biodiesel can be produced by obtaining a material oil by squeezing a seed, and filtering the material oil through a filter. When the *Jatropha* oil is intended to be further purified, for example, it can be purified by distillation, and phorbol ester can be removed by the method described in Japanese Patent Laying-Open No. 2010-209177.

EXAMPLE

Embodiments for carrying out the present invention are described by examples. The following examples do not limit the scope of the present invention.

[Isolation and Identification of Ppat-Encoding DNA in *Jatropha*]

(1) PPAT-Encoding DNA in *Jatropha*

Based on the genome information (contig map) of *Jatropha* mapped in the *Jatropha* genome project that was underwent by Kazusa DNA Res. Inst. and Osaka University with donations from Sumitomo Electric Industries, Ltd., a gene showing homology with *Arabidopsis thaliana* PPAT (At2g18250) was searched by TBLASTN search. As for gene information of PPAT of *Arabidopsis thaliana*, the gene registration information in *Arabidopsis* Information Resource (TAIR) (*arabidopsis*.org/servlets/TairObject?type= locus&name=AT2G18250) was referenced. As a result, it was estimated that there is one clone of a gene sequence encoding PPAT on a genomic DNA sequence of *Jatropha* (Contig 948.1, Contig 6725.1).

(2) Preparation of *Jatropha* Total RNA

Seeds at 4 days from germination of Thailand line of *Jatropha* (*Jatropha curcas*) purchased from Nikko Seed were used. After sterilizing the surface of husked *Jatropha* seeds with 70% ethanol and sodium hypochlorite, the seeds were put on a ½ MS medium, and cultured at 30° C. for 4 days, in a light/dark cycle of 16 hours/8 hours to allow germination. From one germinating seed (about 1 g), a sample containing total RNA was prepared by using Concert Plant RNA Reagent (Invitrogen). Since the prepared sample contained a large amount of oil and fat content, the RNA sample was purified by RNeasy mini column (QIAGEN) for removing this, and total RNA was obtained.

From a mature leaf (1 g) grown from the aforementioned seed of *Jatropha*, a sample containing total RNA was also prepared using Concert™ Plant RNA Reagent (Invitrogen).

(3) Cloning and Amplification of *Jatropha* PPAT cDNA

Using the total RNAs respectively prepared in (2) from germinating seeds and mature leaves as templates, cDNA synthesis by AMV reverse transcriptase was conducted using Reverse Transcription System (Promega). As a primer, Oligo $(dT)_{15}$ (SEQ ID NO: 8) attached to the system was used.

For amplifying a candidate gene encoding PPAT estimated to be present on the genomic DNA sequence, a PCR reaction was conducted using the *Jatropha* cDNA prepared in the above as a template and the following primer set (SEQ ID NOs: 3 and 4), to amplify the target JcPPAT cDNA.

[Chemical formula 2]
Forward primer: 5'-AAAAAGCAGGCTCAAAAATGGCGTTATTAGACGAATCTATGGTTAAT-3'

Reverse primer: 5'-AGAAAGCTGGGTATGCTACTTCTTGTTTTTCACCTTCTCGG-3'

Concretely, to a reaction liquid for PCR shown below was added 1 µL of the *Jatropha* cDNA solution prepared in (1) to make the total amount 20 µL, and a PCR reaction was conducted under the following conditions.

After retaining the reaction liquid at 94° C. for 2 minutes, a cycle of [94° C., 15 seconds→55° C., 30 seconds→68° C., 3 minutes] was repeated 40 times, and then the reaction was cooled to 4° C. The reaction liquid used for PCR is as follows.

| | |
|---|---|
| 0.4 Unit | KOD-plus-polymerase (TOYOBO) |
| 1× | KOD-plus-buffer (TOYOBO) |
| 0.2 mM | dNTPs (TOYOBO) |
| 1 mM | MgSO$_4$ (TOYOBO) |
| 1 µM | Forward primer (SEQ ID NO: 3) |
| 1 µM | Reverse primer (SEQ ID NO: 4) |

After end of the reaction, JcPPAT cDNA obtained by amplification was checked by agarose gel electrophoresis. The result of electrophoresis is shown in FIG. 2. S is a JcPPAT cDNA sample prepared from germinating seeds, L is a JcPPAT cDNA sample prepared from mature leaves, and N is a negative control. A band was observed at approximately 400 to 500 bp which is assumed to be JcPPAT cDNA. The band of the cDNA sample of the germinating seeds was thicker than the band of the cDNA sample of the mature leaves. This implies that the germinating seed expresses more PPAT because it needs to metabolize lipids stored therein actively, and requires a large amount of energy.

[Creation of Vector for Plant Recombination (Construction of Transformation Plasmid)]

For applying the Gateway (registered trade name) cloning system to cDNA amplified in the above, a PCR reaction was conducted for adding adaptor sequences attB1 (SEQ ID NO: 5) and attB2 (SEQ ID NO: 6) shown below.

[Chemical formula 3]
attB1: 5'-GGGGACAAGTTTGTACAAAAAAGCAGGCT-3' attB2: 5'-GGGGACCACTTTGTACAAGAAAGCTGGGT-3'

As a PCR reaction liquid, the one prepared by adding 1 µL of the aforementioned solution of the DNA amplified by PCR to the following solution to make the total amount 50 µL was used.
1 Unit KOD-plus-polymerase (TOYOBO)
1× KOD-plus-buffer (TOYOBO)
0.2 mM dNTPs (TOYOBO)
1 µM attB1_adapter
1 µM attB2_adapter The temperature cycle of the PCR reaction is as follows. After retaining at 94° C. for 1 minute, a cycle of [94° C., 15 seconds→45° C., 30 seconds→68° C., 1 minute] was repeated 5 times, and then a cycle of [94° C., 15 seconds→55° C., 30 seconds→68° C., 1 minute] was repeated 20 times, and then the reaction was cooled to 4° C. After end of the reaction, a PCR product was checked by agarose electrophoresis.

The sequence of a PCR product thus obtained was sequenced by a DNA sequencer. The sequence of the polypeptide coding region was as shown in SEQ ID NO: 2.

The relationship among the *Jatropha* genomic DNA, JcPPAT gene, and primers used in the PCR reaction is as shown in FIG. 3.

DNA represented by SEQ ID NO: 2 was cloned by using a donor vector (pDONR221) of the Gateway (registered trade name) system available from Invitrogen. Concretely, after mixing the JcPPAT gene (having attB1 and attB2 at each end) amplified by PCR and the donor vector pDONR221, a recombination reaction (BP reaction) was conducted using BP clonase (Invitrogen), to obtain pENTRJcPPAT which is to be an entry vector, and then this was introduced into an *Escherichia coli* DH5a strain. pDONR221 has a kanamycin resistant gene introduced as a marker gene.

After extracting the pENTRJcPPAT plasmid from the *Escherichia coli*, and mixing it with a plasmid vector (destination vector) pGWB11 which was made into a straight chain by a restriction enzyme XhoI (TAKARA BIO), a recombination reaction was conducted using LR clonase (Invitrogen).

As shown in FIG. 4, pGWB11 has a 35S promoter as a promoter, and has a FLAG tag added to its C terminal. Also, a 35S promoter -R1-Cmr-ccdB-R2-FLAG is inserted between HindIII and SacI. The part of R1-Cmr-ccdB-R2 can be substituted by attB1-(PPAT)-attB2 by the LR reaction with the entry vector. In this manner, pGWB11 JcPPAT which is to be a vector for plant recombination was obtained.

[Creation of Transformant]

(1) Preparation of *Agrobacterium* for Transformation

The aforementioned vector for recombination was introduced into an *agrobacterium* by an electroporation method to achieve transformation. This transformed *agrobacterium* was shake-cultured in a YEB liquid medium (added with 50 mg/L kanamycin, 50 mg/L hygromycin) at 30° C. for 2 days, and then harvested by centrifugation. The harvested bacterial cells were resuspended in the YEB medium, to prepare a bacterial liquid for infection.

(2) Transformation of *Jatropha*

As a *Jatropha* cell which is to be a host, Thailand line of *Jatropha* (*Jatropha* curcas) which is the same species of *Jatropha* as that used for genome extraction was used. Using mature leaves of the *Jatropha*, transformation was conducted by a leaf disc method. Concretely, first, cut pieces of mature leaves of *Jatropha* which are to be a host (about 25 mm$^2$, hereinafter, referred to as a "*Jatropha* leaf pieces") is sterilized with kitchen bleach that is ×10 diluted with tap water, and kept still at 25° C. for 2 days on a Pre-conditioning agar medium prepared by adding plant hormones (IBA, BA) to a MS basal medium. A bacterial liquid for infection is prepared by suspending an *agrobacterium* in a MS medium, and the aforementioned *Jatropha* leaf pieces are dipped in the bacterial liquid, and shaken for 10 minutes. Then, co-cultivation is conducted on an agar medium at 25° C. for 3 days in a light-shielded environment. As a co-cultivation medium, a Co-cultivation medium prepared by adding acetosyringone to a Pre-conditioning medium is used.

(3) Screening of Transformed *Jatropha*

A transformant having the expression cassette prepared in the above stably inserted into a chromosomal genome of *Jatropha* is screened.

Concretely, *Jatropha* leaf pieces after co-cultivation are washed with an aqueous solution of cefotaxime sodium (200 mg/L), and transformed *Jatropha* (a recombinant cell) is screened. As an antibiotic for screening, kanamycin (20 mg/L) is used. Following transfer to a Shoot regeneration I (SR-I) agar medium, the leaf pieces in which formation of calluses are observed after culturing at 25° C. are transferred to a Shoot regeneration II (SR-II) agar medium.

Next, the selected calluses are transferred to a Shoot elongation I (SE-I) agar medium and a Shoot elongation II (SE-II) agar medium, and an embryoid is allowed to differentiate, and rooting is induced in the R1 agar medium, to obtain a redifferentiated *Jatropha* plant (T1).

Compositions of used media are shown below.

| <MS basal medium> | |
|---|---|
| MS | 1x, (pH 5.8) |
| Sucrose | 3% |
| Myo-inositol | 100 mg/L |
| Thiamine hydrochloride (pH 5.8) | 10 mg/L |
| Agar | 0.8% |
| <½ MS medium> | |
| MS | 0.5x, (pH 5.8) |
| Sucrose | 1.5% |
| Myo-inositol | 50 mg/L |
| Thiamine hydrochloride (pH 5.8) | 5 mg/L |
| Agar | 0.8% |
| <Pre-conditioning medium> MS basal medium | |
| 6-benzylaminopurine (BA) | 1 mg/L |
| 3-indole butyric acid (IBA) | 0.075 mg/L |
| <Co-cultivation medium> MS basal medium | |
| 6-benzylaminopurine (BA) | 1 mg/L |
| 3-indole butyric acid (IBA) | 0.075 mg/L |
| Acetosyringone (AS) | 20 mg/L |
| <SR-I medium> MS basal medium | |
| 6-benzylaminopurine (BA) | 1 mg/L |
| 3-indole butyric acid (IBA) | 0.075 mg/L |
| Cefotaxime sodium | 200 mg/L |
| Kanamycin | 20 mg/L |
| <SR-II medium> MS basal medium | |
| 6-benzylaminopurine (BA) | 3 mg/L |
| 3-indole butyric acid (IBA) | 0.5 mg/L |
| Cefotaxime sodium | 200 mg/L |
| Kanamycin | 20 mg/L |
| <SE-I medium> MS basal medium | |
| 6-benzylaminopurine (BA) | 2 mg/L |
| Cefotaxime sodium | 200 mg/L |
| Kanamycin | 20 mg/L |
| <SE-II medium> MS basal medium | |
| 6-benzylaminopurine (BA) | 2 mg/L |
| Kanamycin | 20 mg/L |
| <RI medium> MS basal medium (MS of ½ concentration) | |
| 3-indole butyric acid (IBA) | 0.2 mg/L |

(4) Confirmation of JcPPAT Gene Expression

It is checked that PPAT is overexpressed in a transformant selected by the screening.

After culturing a transformed cell (a transformed dicot cell that expresses a PPAT polypeptide by a promoter), and a control (a dicot cell of wild-type *Jatropha*), mRNA is extracted, and amplified by a RT-PCR reaction using a nucleotide represented by SEQ ID NO: 1 as a template, and the amount of mRNA of JcPPAT is quantified, and compared with the control.

[Creation of Transformed *Jatropha* and Confirmation of Viability]

An embryoid induced from a transformed callus having a JcPPAT gene introduced therein is transferred to a R1 medium and allowed to root, to create a redifferentiated *Jatropha* plant (T1).

In creation, the length of root of the rooting, area of leaf, and concentration of coenzyme A are measured and compared with those of the wild type.

Also, the plantlet obtained by redifferentiation is sand cultured, and cultured under a water deficient condition after irrigation is stopped at an arbitrary point of time, and the photosynthetic rate and chlorophyll fluorescence, transpiration rate, and yellowing, curling and falling of mature leaves of the plantlett are compared with those of the wild type, and dry stress resistance is evaluated.

INDUSTRIAL APPLICABILITY

The novel polynucleotide and so on of the present invention can be used for creation of growth-enhanced *Jatropha* and dry stress resistant *Jatropha*. Also, they may be used for creation of *Jatropha* breeds with an increased fatty acid content and a modified fatty acid composition of a seed.

The invention claimed is:

1. A vector comprising:
   (a) a cDNA comprising the polynucleotide represented by SEQ ID NO: 2 or
   (b) a polynucleotide encoding a phosphopantetheine adenylyltransferase (PPAT) polypeptide having a homology of 95% or higher with the amino acid sequence of SEQ ID NO: 1, wherein said polynucleotide is operably linked to a heterologous regulatory element.

2. A cDNA comprising the polynucleotide represented by SEQ ID NO: 2.

3. An isolated PPAT polypeptide other than the polypeptide of SEQ ID NO: 1, wherein said polypeptide has an amino acid sequence having a homology of 95% or higher with the amino acid sequence of SEQ ID NO: 1, and wherein the polypeptide catalyzes an exchange reaction between 4'-phosphopantetheine and dephospho-coenzyme A.

4. A polynucleotide encoding the polypeptide according to claim 3.

5. A The vector according to claim 1, wherein said vector is a *Jatropha* plant transformation vector.

6. A transformant containing the vector according to claim 5.

7. A transgenic *Jatropha* plant transformed with the vector according to claim 5, wherein said transgenic plant has increased stress tolerance when compared to a corresponding control *Jatropha* plant.

8. A transgenic seed harvested from the stress resistant transgenic *Jatropha* plant according to claim 7, wherein the seed comprises the vector.

9. A method of producing a *Jatropha* oil, comprising: squeezing the seed according to claim 8 to obtain a material oil, and purifying the material oil.

10. A method of producing a stress resistant *Jatropha* plant, comprising:
   producing an isolated polynucleotide selected from the following polynucleotides:
      (a) a cDNA comprising the polynucleotide represented by SEQ ID NO: 2; or
      (b) a polynucleotide encoding a PPAT polypeptide having a homology of 95% or higher with the amino acid sequence of SEQ ID NO: 1;
   producing a *Jatropha* plant transformation vector comprising said isolated polynucleotide; and
   transforming a *Jatropha* plant with said vector.

\* \* \* \* \*

UNITED STATES PATENT AND TRADEMARK OFFICE
CERTIFICATE OF CORRECTION

PATENT NO.        : 9,255,278 B2
APPLICATION NO.   : 13/643396
DATED             : February 9, 2016
INVENTOR(S)       : Kiichi Fukui et al.

It is certified that error appears in the above-identified patent and that said Letters Patent is hereby corrected as shown below:

In The Claims

In column 17, line 6 (claim 5, line 1) please change "A The vector according to claim 1" to
-- The vector according to claim 1 --.

Signed and Sealed this
Twenty-third Day of August, 2016

Michelle K. Lee
*Director of the United States Patent and Trademark Office*

SEQUENCE LISTING

<160> NUMBER OF SEQ ID NOS: 8

<210> SEQ ID NO 1
<211> LENGTH: 174
<212> TYPE: PRT
<213> ORGANISM: Jatropha curcas

<400> SEQUENCE: 1

```
Met Ala Leu Leu Asp Glu Ser Met Val Asn Trp Thr Ile Ser Pro Pro
1               5                  10                  15

Asn Thr Tyr Gly Ala Val Val Leu Gly Gly Thr Phe Asp Arg Leu His
            20                  25                  30

Asp Gly His Arg Leu Phe Leu Lys Ala Ser Ala Glu Leu Ser Arg Asp
        35                  40                  45

Arg Ile Val Ile Gly Val Cys Asp Gly Pro Met Leu Thr Lys Lys Gln
    50                  55                  60

Phe Ala Asp Leu Ile Gln Pro Ile Glu Glu Arg Met Arg Asn Val Glu
65                  70                  75                  80

Asn Tyr Ile Lys Ser Ile Lys Pro Glu Leu Ala Val Gln Val Glu Pro
                85                  90                  95

Ile Val Asp Pro Tyr Gly Pro Ser Ile Val Asp Glu Asn Leu Glu Ala
            100                 105                 110

Ile Val Val Ser Lys Glu Thr Val Pro Gly Gly Leu Ser Val Asn Lys
        115                 120                 125

Lys Arg Ala Glu Lys Gly Leu Pro Leu Leu Lys Ile Glu Val Val Asp
    130                 135                 140

Leu Leu Ser Glu Gly Ser Asn Gly Asp Lys Leu Ser Ser Thr Thr Leu
145                 150                 155                 160

Arg Arg Leu Glu Ala Glu Lys Val Lys Lys Gln Glu Val Ala
                165                 170
```

<210> SEQ ID NO 2
<211> LENGTH: 525
<212> TYPE: DNA
<213> ORGANISM: Jatropha curcas

<400> SEQUENCE: 2

```
atggcgttat tagacgaatc tatggttaat tggacgatat caccgcctaa tacatatggt    60
gcggtggttc tcggcggcac cttcgaccga ttacatgacg gccatcgcct ttttctaaag   120
gcatcggcag agctgtctag ggatcgaatt gttattggag tttgcgatgg tcccatgtta   180
actaagaagc agtttgctga cttaatacag cccattgaag aaaggatgcg aaatgttgaa   240
aattacatca agtccattaa accagaactt gctgtgcaag ttgaacctat cgttgatccc   300
tatggacctt caatcgttga tgaaaatttg gaggctatag ttgtaagcaa ggagacagtg   360
ccaggtgggc tgtcagtcaa taagaagagg gctgagaaag gactcccact tctaaagatt   420
gaagtcgtgg atctactttc agaaggatct aatggtgata agctcagttc caccacatta   480
aggaggctcg aggccgagaa ggtgaaaaaa caagaagtag catga               525
```

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 3
aaaaagcagg ctcaaaaatg gcgttattag acgaatctat ggttaat        47

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agaaagctgg gtatgctact tcttgttttt tcaccttctc gg             42

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggggacaagt ttgtacaaaa aagcaggct                            29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggggaccact ttgtacaaga aagctgggt                            29

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tttttttttt ttttt                                           15
```